US006358528B1

(12) United States Patent
Grimmett et al.

(10) Patent No.: US 6,358,528 B1
(45) Date of Patent: Mar. 19, 2002

(54) PHARMACEUTICAL FORMULATION

(75) Inventors: Francis Walter Grimmett, Rustington (GB); Nigel Philip McCreath Davidson, Bristol, TN (US)

(73) Assignee: SmithKline Beecham p.l.c. (GB)

( * ) Notice: Subject to any disclaimer, the term of this patent is extended or adjusted under 35 U.S.C. 154(b) by 0 days.

(21) Appl. No.: 09/640,823

(22) Filed: Aug. 17, 2000

Related U.S. Application Data

(62) Division of application No. 08/718,550, filed as application No. PCT/EP95/01269 on Apr. 7, 1995, now Pat. No. 6,136,345.

(30) Foreign Application Priority Data

Apr. 14, 1994 (GB) ............................................... 9407386

(51) Int. Cl.⁷ ............................ A61K 9/24; A61K 9/32; A61K 9/36

(52) U.S. Cl. ..................... 424/474; 424/471; 424/472; 424/480; 424/482

(58) Field of Search ................................ 424/482, 480, 424/471, 472, 474

(56) References Cited

U.S. PATENT DOCUMENTS

| 3,279,997 A | 10/1966 | Schneyer |
| 4,525,339 A | 6/1985 | Behl et al. .................... 424/16 |
| 4,775,536 A | 10/1988 | Patell ......................... 424/471 |
| 4,966,772 A | 10/1990 | Ohm et al. ................. 424/482 |
| 5,158,777 A | 10/1992 | Abramowitz et al. ....... 424/458 |
| 5,277,916 A | 1/1994 | Dwyer et al. ............... 424/494 |
| 5,407,686 A | 4/1995 | Patel et al. ................. 424/468 |
| 5,558,879 A | 9/1996 | Chen et al. ................. 424/480 |
| 5,910,322 A | 6/1999 | Rivett et al. |
| 6,051,255 A | 4/2000 | Conley et al. |

FOREIGN PATENT DOCUMENTS

| WO | WO 94/06416 | 3/1994 | ........... A61K/9/24 |
| WO | WO 94/27557 | 12/1994 | |
| WO | WO 95/20946 | 8/1995 | |
| WO | WO 96/04907 | 8/1995 | |

Primary Examiner—Edward J. Webman
(74) Attorney, Agent, or Firm—Dara L. Dinner; Stephen Venetianer; Charles M. Kinzig

(57) ABSTRACT

A tablet formulation which comprises a core containing a pharmaceutically active material containing amoxycillin and clavulanate, coated with a release retarding coating, surrounded by a casing layer which includes a second pharmaceutically active material containing amoxycillin and clavulanate.

42 Claims, 1 Drawing Sheet

PHARMACEUTICAL FORMULATION

This application is a division of Ser. No. 08/718,550 filed Nov. 25, 1996, now U.S. Pat. No. 6,136,345 which is a 371 of PCT/EP95/01269 filed Apr. 7, 1995.

This invention relates to tablet formulations for oral administration, particularly to formulations, which comprise a β-lactam antibiotic, optionally together with a β-lactamase inhibitor.

Many known tablet formulations which include a β-lactam antibiotic are required to be taken orally three times a day. There is a need for oral formulations which need only be taken twice or less often per day. Methods of forming delayed or sustained release tablet formulations are known, for example coating the tablet with a release-retarding coating, or coating individual granules with such a coating, and compressing these coated granules into a tablet. "Release-retarding" as used herein, unless otherwise defined, refers both to release which is retarded so as to be sustained, i.e. active material is released gradually from the tablet, and to release which is retarded so as to be delayed, i.e. release begins or the rate of release increases after an initial delay.

Particular problems occur in the preparation of delayed or sustained release forms of the known antibacterial combination of the β-lactam antibiotic amoxycillin, in the form of its trihydrate, and the β-lactamase inhibitor clavulanic acid, in the form of an alkali metal salt, such as potassium clavulanate. This is because amoxycillin trihydrate is relatively insoluble in aqueous media, whereas potassium clavulanate is extremely soluble, hygroscopic and moisture-sensitive, and it is difficult to achieve sustained or delayed release of two such components at a compatible rate from a single formulation containing both.

According to this invention, a tablet formulation comprises a core which includes a first pharmaceutically active material, the core being coated with a release retarding coating, the coated core being itself surrounded by a casing layer which includes a second pharmaceutically active material.

The tablet formulation of the invention is suitable for oral administration, and provides a sustained and/or delayed release as a result of initial quick release of the second active material from the casing layer, and a sustained or delayed release of first active material from the coated core. Also the casing layer may serve to protect the core from the ingress of air and atmospheric moisture. Also coating of a single relatively large core in the tablet of the invention with a release-retarding coating requires less coating material than is required to coat a large number of smaller granules, and can therefore lead to a relatively low tablet weight.

The first and second pharmaceutically active materials in the tablet formulation may each individually, and/or together, comprise a β-lactam antibiotic optionally together with a β-lactamase inhibitor. Suitably the β-lactam antibiotic may be amoxycillin, e.g. in the form of its trihydrate, optionally together in combination with the β-lactamase inhibitor clavulanate, (the term "clavulanate" used herein, unless otherwise identified, refers both to clavulanic acid and its salts) e.g. in particular potassium clavulanate. The first and second active materials may both comprise the same active material, for example both comprising a β-lactam antibiotic optionally in combination with a β-lactamase inhibitor. When both the first and second active materials comprise amoxycillin and clavulanate, the relative ratios of amoxycillin:clavulanate may be different in the core and the casing layer, making up the overall ratio in the tablet.

The amoxycillin:clavulanate ratios in the core and casing layer and the overall ratio may each vary between broad limits, e.g. between 30:1 to 1:1, typically 12:1 to 2:1. A preferred ratio is around 8:1 to 4:1±25%.

The quantity of active material(s) in the tablet may vary up to the maximum allowed daily dose, and may typically be around a nominal single unit dose. For example in the case of amoxycillin and clavulanate, a single tablet may contain around 125, 250, 500, 750 or 875 mg of amoxycillin, and 62.5, 125 or 250 mg of clavulanate, both sets of weights being expressed in terms of the respective free acids. Typically the overall tablet may contain nominally 500 mg amoxycillin and 125 mg clavulanate, or 875 mg amoxycillin and 125 mg of clavulanate. Alternatively these weights may be divided between two or more tablets.

Typically for example the core may contain 25–75% of the total weight of the first and second components, and the casing layer may contain 75–25% thereof.

In the case of amoxycillin and clavulanate, in one embodiment both the core and the casing layer may contain clavulanate and amoxycillin. For example the core may contain 25–75% of the clavulanate and 25–75% of the amoxycillin, the balance being contained in the casing layer. For example the core may contain 100–400 mg of amoxycillin and 30–95 mg of clavulanate, expressed as the respective free acids. In an alternative embodiment, all of the clavulanate may be contained in the casing layer, e.g. in a rapid release form, with none of the clavulanate contained in the core. Such an embodiment may assist in maximising the clavulanate plasma level peak. In another alternative embodiment, all of the clavulanate may be contained in the core, with none of the clavulanate contained in the casing layer.

The core may be any convenient shape and need not necessarily be directly related to the shape of the overall tablet, typically the core may be spherical, ellipsoidal, or oblate spheroidal, within any suitable or convenient, e.g. a conventional, tablet shape.

The core and the casing layer may both comprise a compact of compressed ingredients including the respective active materials such as amoxycillin trihydrate optionally combined with potassium clavulanate. The active material (s) in the core may be present in a micronised or solubilised form. In addition to active materials the core and casing layer may contain additives conventional to the art of compressed tablets. Appropriate additives in such a tablet may comprise diluents such as calcium carbonate, magnesium carbonate, dicalcium phosphate or mixtures thereof, binders such as microcrystalline cellulose hydroxypropylmethylcellulose, hydroxypropyl- cellulose, polyvinylpyrrolidone, pre-gelatinised starch or gum acacia or mixtures thereof, disintegrants such as microcrystalline cellulose (fulfilling both binder and disintegrant functions) cross-linked polyvinylpyrrolidone, sodium starch glycollate, croscarmellose sodium or mixtures thereof, lubricants, such as magnesium stearate or stearic acid, glidants or flow aids, such as colloidal silica, talc or starch, and stabilisers such as desiccating amorphous silica, colouring agents, flavours etc. The core and casing layer may contain the same or different additives, in the same or different proportions.

The core may be made from a compacted mixture of its components, suitably in the form of granules, which may be made by a conventional granulating process as known in the art. Preferably the granules are made by a procedure of dry granulation of the granule components, for example milling, blending, slugging then milling, or by milling, blending or roller compaction then milling. The granules may include conventional additives introduced as a result of the granulation process, e.g. lubricants such as magnesium stearate, in conventional quantities, e.g. ca. 0.5–1 wt % of magnesium stearate. Suitably the granules are of 10–80 mesh size, suitably 10–40 mesh size, for example 16–30 mesh size.

The release-retarding coating may be a polymeric material, for example an enteric polymer (the term "enteric polymer" is a term of the art referring to a polymer which is preferentially soluble in the less acid environment of the intestine relative to the more acid environment of the stomach).

An enteric coating may be an essentially conventional coating material, for example enteric polymers such as cellulose acetate phthalate, cellulose acetate succinate, methylcellulose phthalate, ethylhydroxycellulose phthalate, polyvinylacetatephthalate, polyvinylbutyrate acetate, vinyl acetate-maleic anhydride copolymer, styrene-maleic monoester copolymer, methyl acrylate-methacrylic acid copolymer, methacrylate-methacrylic acid-octyl acrylate copolymer, etc. These may be used either alone or in combination, or together with other polymers than those mentioned above. The enteric coating may also include insoluble substances which are neither decomposed nor solubilized in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional crosslinking agents such as epichlorohydrin, dichlorohydrin, 1, 2-, 3, 4-diepoxybutane, etc. The enteric coating may also include starch and/or dextrin.

Preferred coating materials are the pharmaceutically acceptable methacrylic acid copolymer which are copolymers, anionic in character, based on methacrylic acid and methyl methacrylate, for example having a ratio of free carboxyl groups: methyl-esterified carboxyl groups of 1:>3, e.g. around 1:1 or 1:2, and with a mean molecular weight of 135000.

Such polymers are sold under the trade name Eudragit™, such as the Eudragit L series e.g. Eudragit L 12.5™, Eudragit L 12.5P™, Eudragit L100™, Eudragit L 100-55™, Eudragit L-30™, Eudragit L-30 D-55™, the Eudragit S™ series e.g. Eudragit S 12.5, Eudragit S 12.5P™, Eudragit S100™, the Eudragit NE™ series e.g. Eudragit NE 30D™, the Eudragit RL™ series, e.g. Eudragit RL 12.5™, Eudragit RL 100™, Eudragit RL PO™, Eudragit RL 30D ™, and the Eudragit RS™ series e.g. Eudragit RS 12.5™, Eudragit RS 100™, Eudragit RS PO™, and Eudragit RS 30D™.

Some of these polymers are known and sold as enteric polymers, for example having a solubility in aqueous media at pH 5.5 and above, such as the commercially available "Eudragit" (Trade Mark) enteric polymers, such as "Eudragit L 30" (Trade Mark) i.e. a cationic polymer synthesised from dimethylaminoethyl methacrylate, "Eudragit S" (Trade Mark) and "Eudragit NE" (Trade Mark).

Such polymers may be used either alone or with a plasticiser. Such coatings are normally applied using a liquid medium, and the nature of the plasticiser depends upon whether the medium is aqueous or non-aqueous. Aqueous plasticisers include propylene glycol or "Citroflex" or Citroflex A2" (Trade Marks) (mainly triethyl citrate or acetyl triethyl citrate). Non-aqueous plasticisers include these, and also diethyl and dibutyl phthalate and dibutyl sebacate.

The quantity of plasticiser included will be apparent to those skilled in the art. The enteric coating may also include an anti-tack agent such as talc, silica or glyceryl monostearate. The quantity of plasticiser and anti-tack agent may be generally conventional to the art. Typically the coating may include around 10–25 wt. % plasticiser and up to around 50 wt % of anti tack agent, e.g. 5–20 wt. % of anti-tack agent.

An enteric coating may be applied to the core by dissolving or suspending the enteric coating materials in a suitable medium, such as water, methanol, ethanol, isopropanol, acetone, methyl ethyl ketone, methylene chloride, ethylene chloride, ethyl acetate, etc. or mixtures thereof, and the resultant solution or suspension may be sprayed on the core to coat them, followed by drying sufficiently with an air flow and screening.

In the case of the preferred enteric coating material referred to above, the enteric coating material may be dissolved or suspended in a solvent for example water and coated onto the core using a fluidised bed system. If water is used, preferably an anti-foaming agent such as activated polymethylsiloxane is also included.

It may be desirable, particularly in the case of cores which contain highly soluble or moisture sensitive active materials such as potassium clavulanate, to first apply one or more sub-coats to the core, before application of the release retarding coating layer, the sub-coat consequently lying beneath the release retarding coating. Suitable sub-coat materials include hydroxypropylmethyl cellulose, for example of the known types E5 and E15 (Trade Marks) in mixture. It may also be desirable to apply one or more over-coats after application of the release retarding coating layer, the over-coat consequently lying over the release retarding coating. Suitable over-coat materials include copolymers of methacrylic acid and methyl methacrylate, and hydroxypropylmethyl cellulose. The over-coat may be of the same material as the sub-coat. Typically such coatings may be applied by known techniques of aqueous film coating.

The casing layer may be applied to the coated core by a generally conventional process in which the coated core is encased in a mass of the powdered or granulated casing material components. The granules of such a casing material may be made by a conventional granulating process as known in the art, and as discussed above with reference to the manufacture of the core granules.

The casing layer itself may be coated with a final outer coating, for example of hydroxypropyl methyl cellulose, which may be applied by known film coating techniques in a similar manner to the way in which the sub-and over-coats may be applied to the core.

The tablet of the invention offers the advantages effect that the active material in the casing layer is released initially in the stomach, and the coated core releases its active material content more slowly. In this way as in vivo decay of the initially released material occurs, active material is subsequently released from the core to provide an extended blood level profile. If the release-retarding coating on the core is an enteric coating the release of active material from the core may occur in the intestine.

The invention therefore also provides a method of preparing a pharmaceutical formulation as described herein, comprising the steps of forming a core which includes a first pharmaceutically active material, the core being coated with a release-retarding coating, then coating the core with a casing layer which includes a second pharmaceutically active material.

Clavulanic acid and its derivatives, e.g. salts such as potassium clavulanate are extremely moisture sensitive, and all operations carried out to prepare granules and formulations of this invention which contain clavulanate should be carried out under conditions of low relative humidity, e.g. less than 30% RH, ideally as low as practical.

The present invention also provides a pharmaceutical formulation as described herein for use as an active therapeutic substance.

The present invention also provides a pharmaceutical formulation as described herein for use in the treatment of bacterial infections.

The present invention also provides the use of a formulation as described herein in the manufacture of a medicament for use in the treatment of bacterial infections.

The present invention also provides a method of treatment of bacterial infections in humans or animals which comprises the administration of an effective amount of a pharmaceutical formulation as described herein.

BRIEF DESCRIPTION OF THE DRAWING

The invention will now be described by way of example only, with reference to FIG. 1 which shows a cross-section through a tablet of the invention.

EXAMPLE 1

Figure 1:
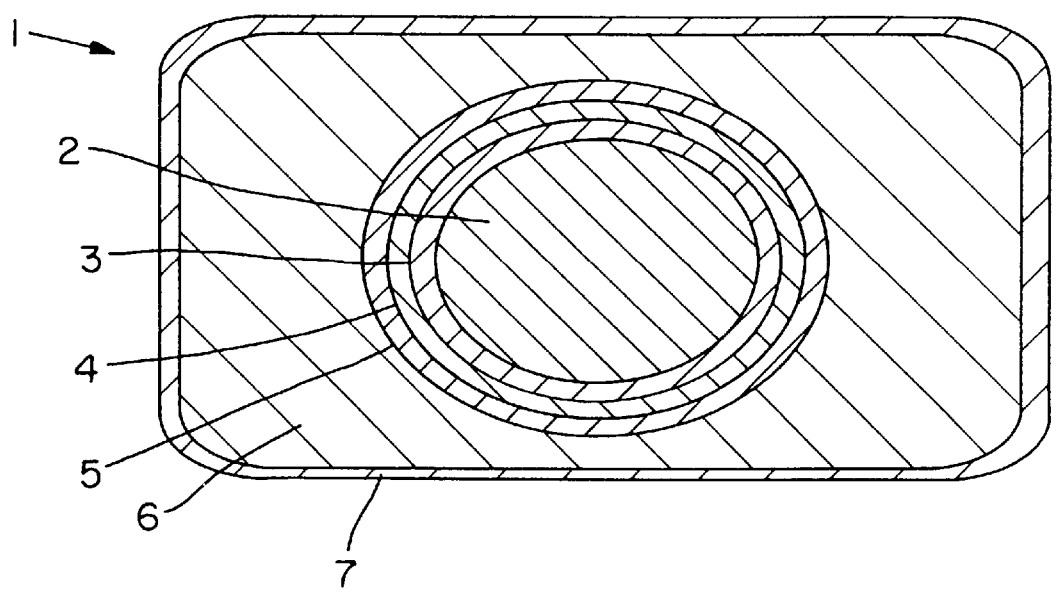
Referring to FIG. 1, a tablet (overall (1)) comprises a core (2), which is coated with successively a sub-coat (3), an enteric coat (4), and an over-coat (5). The coated core (2–5) is itself encased within a casing layer (6) forming the overall shape of the tablet (1), and the casing layer (6) is itself coated with a protective film coat (7). The relative sizes of the core (2) and tablet (1), and the thickness of the coating layers (3), (4), (5), (6), (7) are not to scale but merely illustrative.

Tablets 1 and 2 were prepared respectively being tablets containing nominally 500 mg and 875 mg of amoxycillin as the trihydrate, both tablets containing 125 mg of clavulanate, as potassium clavulanate.

Core

The core for tablets 1 and 2 had the same composition and was made by the same procedure. Their formulation was as below:

| Component | mg | % | % Range* (mg range) |
|---|---|---|---|
| Amoxycillin trihydrate equivalent to Amoxycillin | 250 | 55.56 | 22.2–88.8 (100 mg–400 mg) |
| Potassium Clavulanate equivalent to Clavulanic Acid | 62.5 | 13.90 | 6.94–20.8 (30 mg–95 mg) |
| Polyplasdone XL dried | 23.0 | 5.10 | 1.0–20.0 |
| Syloid AL1 | 23.0 | 5.10 | 1.0–20.0 |
| Magnesium Stearate | 4.5 | 1.0 | 0.2–2.0 |
| Microcrystalline Cellulose to | 450.0 | 100.0 | 400 mg–900 mg |

The Polyplasdone XL dried is present as a disintegrant. The Syloid AL1 is a desiccant to prevent hydrolytic degradation of the actives. The magnesium stearate is present as a lubricant. The microcrystalline cellulose is a tablet binder and disintegrant.

The cores were made by the following process:
1. Granulation
1.1 The amoxycillin trihydrate was milled using a swing hammer mill at fast speed through a 0.063" screen with knives forward.
1.2 The milled amoxycillin trihydrate was mixed with the potassium clavulanate, Polyplasdone, Syloid AL1, part of the magnesium stearate, and part of the microcrystalline cellulose.
1.3 The blend from 1.2 was slugged or roller compacted
1.4 The compacts or flake from 1.3 was milled through a swing hammer mill at medium speed with knives forward and fitted with an 0.063" screen.
2. Compaction

| | % |
|---|---|
| Compacted Granules from 1.4 | 94.5 |
| Magnesium Stearate | 0.5 |
| Microcrystalline Cellulose | 5.0 |

2.1 Granules from 1.4 were blended with remaining Magnesium Stearate and remaining Microcrystalline cellulose.
2.2. The cores were manufactured from the compression mix prepared in 2.1 to a core weight of 450 mg, and a hardness of 15–20 Kp Schleuniger.
2.3 The cores were then film sub-coated with an aqueous suspension of hydroxypropyl methyl cellulose, further coated with an Eudragit enteric coating and finally, with a further over-coating of hydroxypropyl methyl cellulose.

Hydroxypropl Methyl Cellulose Core Subcoat and Over Coat

| | % |
|---|---|
| Hydroxypropl methyl cellulose E5 | 4.95 |
| Hydroxypropl methyl cellulose E15 | 1.65 |
| Polyethylene Glycol 6000 | 0.98 |
| Polyethylene Glycol 4000 | 0.98 |
| Titanium Dioxide | 6.45 |
| Purified Water PhEur to | 100.0 |

A coat weight of 18 mg was applied to the core.
Eudragit Film Coat Formula

| | % |
|---|---|
| Eudragit L30D (Trade Mark) | 15.00 |
| Antifoam M (Trade Mark) | 0.15 |
| Acetyl Triethyl Citrate | 2.25 |
| Talc Micronised | 3.00 |
| Pumped Water to | 100.00 |

An enteric coat weight of 21.2 mg was applied to the core. A 5 mg/tablet final over-coat of the cores with a hydroxypropyl methyl cellulose coating was applied. The three film coats were applied to the core using low humidity conditions to effect rapid drying, in a coating drum (Accelacota, Driam or Hicota), using an intermittent air spray process.
Preparation of tablets incorporating cores from above.
Tablet 1
500 mg of Amoxycillin as Amoxycillin Trihydrate.
125 mg Clavulanic Acid as Potassium Clavulanate.

| Component | mg/tab | % |
|---|---|---|
| Amoxycillin trihydrate equivalent to Amoxycillin | 250 | 39.30 |
| Potassium Clavulanate equivaient to Clavulanic Acid | 62.5 | 9.83 |
| Polyplasdone XL (TM) dried | 23.0 | 3.62 |

-continued

| Component | mg/tab | % |
|---|---|---|
| Syloid AL1 (Trade Mark) | 23.0 | 3.62 |
| Magnesium Stearate | 4.5 | 0.71 |
| Microcrystalline Cellulose to | 635.8 | 100.0 |

The casing layer was applied to the cores by the following process:
1. Granulation of Casing Material
1.1 The amoxycillin trihydrate was milled using a swing hammer mill at fast speed through an 0.063 inch screen with knives forward.
1.2 The amoxycillin trihydrate was blended with the potassium clavulanate, Polyplasdone, Syloid AL1 and part of the magnesium stearate and part of the microcrystaline cellulose.
1.3 The blend from 1.2 was slugged or roller compacted.
1.4 The compacts or flake from 1.3 were milled through a swing hammer mill operating at medium speed with knives forward and fitted with a 0.063" screen.
1.5 The granules from 1.4 were blended with the remaining magnesium stearate and remaining microcrystalline cellulose.
2. Application of Casing Layer

|  | Per Tablet (mg) |
|---|---|
| Enteric coated core (film coated) | 494.2 |
| Compression mix (tablet casting) | 635.8 |
| Tablet weight | 1130.0 |
| Hydroxypropl Methyl Cellulose film coat | 27.0 |
| Film coat Tablet | 1157.0 |

The cores were fed to a specially designed tablet press, e.g. a Kilian RX machine adapted for core tablet manufacture, which dosed the compression mix 'tablet casing' and a core into the tablet die followed by a further quantity of compression mix 'tablet casing' and the total core/compression mix was compressed to form a 1130 mg tablet. The tablet press was designed to reject tablets which do not contain a core. Alternatively individual tablets could be made by hand.

The tablet was aqueous film coated using a Hydroxypropl Methyl Cellulose aqueous film coat, applying 27 mg of coat to the tablet. This process was carried out in a coating drum, e.g. Accelacota, Driam or Hicota, using an air spray process.
Tablet 2
875 mg amoxycillin as amoxycillin trihydrate
125 mg of clavulanic acid as potassium clavulanate

| Casing Layer Components | mg/tab | % |
|---|---|---|
| Amoxycillin trihydrate equivalent to Amoxycillin | 625.0 | 78.13 |
| Potassium Clavulanate equivalent to Clavulanic Acid | 62.5 | 7.81 |
| Polyplasdone XL dried | 23.0 | 2.88 |
| Syloid AL1 | 23.0 | 2.88 |
| Magnesium Stearate | 4.05 | 0.51 |
| Microcrystalline Cellulose to | 800.0 to | 100 |

The casing layer material was prepared by a slugging or roller compaction process as described with respect to Tablet 1 above.
2. Application of Casing Layer

|  | Per Tablet (mg) |
|---|---|
| Enteric coated core (film coated) as described for Presentation 1 | 494.2 |
| Compression mix (tablet casing) | 800.0 |
| Tablet weight | 1294.2 |
| Hydroxypropl Methyl Cellulose film coat | 32.0 |
| Film coat Tablet | 1326.2 |

The compression mix and cores were fed to a designed core tablet press equipped to reject tablets which do not contain a core. Alternatively tablets could be made individually by a hand press.

The tablets each containing a core were aqueous film coated in a drum coating unit, e.g. an Accelacota, Driam or Hicota with a Hydroxypropl Methyl Cellulose Suspension to a film coat weight of 32 mg.

What is claimed is:

1. A tablet formulation for oral administration comprising amoxycillin and clavulanate in a ratio of 30:1 to 1:1 in which 25 to 75% of the total weight of amoxycillin and 25 to 75% of the total weight of clavulanate is in a central core which is surrounded by a release-retarding coating layer which is an enteric polymer coating, and a casing layer surrounding the core containing from 75 to 25% of amoxycillin and from 75 to 25% of clavulanate, such that there is an initial quick release of amoxycillin and clavulanate from the casing layer and a sustained release of amoxycillin and clavulanate from the core.

2. A tablet formulation according to claim 1 wherein the core and the casing layer both comprise a compacted mixture of components.

3. A tablet formulation according to claim 1 further comprising one or more sub-coats beneath the release retarding coating layer.

4. A tablet formulation according to claim 1 further comprising one or more over-coats above the release retarding coating layer.

5. A tablet formulation according to claim 1 for oral administration twice a day.

6. A method of treating a bacterial infection in a patient in need thereof, which method comprises administering to said patient an effective amount of a formulation according to claim 1.

7. A tablet formulation according to claim 1 wherein the total weight of amoxycillin is from 50 to 75% in the central core.

8. A tablet formulation according to claim 1 wherein the total weight of amoxycillin is from 50 to 25% in the casing layer.

9. A tablet formulation according to claim 1 wherein the total weight of clavulanate is from 50 to 75% in the central core.

10. A tablet formulation according to claim 1 wherein the total weight of clavulanate is from 50 to 25% in the casing layer.

11. A tablet according to claim 1 wherein the enteric polymer coating is cellulose acetate phthalate, cellulose acetate succinate, methylcellulose phthalate, ethylhydroxycellulose phthalate, polyvinylacetatephthalate, polyvinylbutyrate acetate, vinyl acetate-maleic anhydride copolymer, styrene-maleic mono-ester copolymer, methyl acrylate-methacrylic acid copolymer, or methacrylate-methacrylic acid-octyl acrylate copolymer, or a mixture thereof.

12. A tablet according to claim 1 wherein the enteric polymer coating is a methacrylic acid—methacrylate copolymer.

13. A tablet according to claim 1 wherein the enteric polymer coating further comprises a plasticiser.

14. A tablet according to claim 1 wherein the enteric polymer coating further comprises an anti-foaming agent.

15. A tablet according to claim 1 wherein the enteric polymer coating further comprises an anti-tack agent.

16. A tablet according to claim 1 wherein the amoxycillin is amoxycillin trihydrate.

17. A tablet according to claim 1 wherein the clavulanate is potassium clavulanate.

18. A tablet according to claim 2 wherein the sub-coat is hydroxypropylmethylcellullose.

19. A tablet according to claim 3 wherein the over-coat is hydroxypropylmethylcellullose, or a co-polymer of methacrylic acid and methyl methacrylate.

20. A tablet according to claim 1 wherein the casing layer is coated with a top coat.

21. A tablet according to claim 20 wherein the top coat is hydroxypropylmethylcellulose.

22. A tablet formulation for oral administration comprising amoxycillin and clavulanate in a ratio of 30:1 to 1:1 in which 25 to 75% of the total weight of amoxycillin and 25 to 75% of the total weight of clavulanate is in a central core which is surrounded by a release-retarding coating layer which is an enteric polymer coating, and a casing layer surrounding the core containing from 75 to 25% of amoxycillin and from 75 to 25% of clavulanate, such that there is an initial quick release of amoxycillin and clavulanate from the casing layer and a delayed release of amoxycillin and clavulanate from the core.

23. A tablet formulation according to claim 22 wherein the total weight of amoxycillin is from 50 to 75% in the central core.

24. A tablet formulation according to claim 22 wherein the total weight of amoxycillin is from 50 to 25% in the casing layer.

25. A tablet formulation according to claim 22 wherein the total weight of clavulanate is from 50 to 75% in the central core.

26. A tablet formulation according to claim 22 wherein the total weight of clavulanate is from 50 to 25% in the casing layer.

27. A tablet according to claim 22 wherein the enteric polymer coating is cellulose acetate phthalate, cellulose acetate succinate, methylcellulose phthalate, ethylhydroxycellulose phthalate, polyvinylacetatephthalate, polyvinylbutyrate acetate, vinyl acetate-maleic anhydride copolymer, styrene-maleic mono-ester copolymer, methyl acrylate-methacrylic acid copolymer, or methacrylate-methacrylic acid-octyl acrylate copolymer, or a mixture thereof.

28. A tablet according to claim 22 wherein the enteric polymer coating is a methacrylic acid—methacrylate copolymer.

29. A tablet according to claim 22 wherein the enteric polymer coating further comprises a plasticiser.

30. A tablet according to claim 22 wherein the enteric polymer coating further comprises an anti-foaming agent.

31. A tablet according to claim 22 wherein the enteric polymer coating further comprises an anti-tack agent.

32. A tablet according to claim 22 wherein the amoxycillin is amoxycillin trihydrate.

33. A tablet according to claim 22 wherein the clavulanate is potassium clavulanate.

34. A tablet according to claim 22 further comprising one or more sub-coats beneath the release retarding coating layer.

35. A tablet according to claim 34 wherein the sub-coat is hydroxypropylmethylcellullose.

36. A tablet according to claim 22 further comprising one or more over-coats over the release retarding coating layer.

37. A tablet according to claim 36 wherein the over-coat is hydroxypropylmethylcellullose, or a co-polymer of methacrylic acid and methyl methacrylate.

38. A tablet according to claim 22 wherein the casing layer is coated with a top coat.

39. A tablet according to claim 38 wherein the top coat is hydroxypropylmethylcellulose.

40. A tablet formulation according to claim 22 wherein the core and the casing layer both comprise a compacted mixture of components.

41. A tablet formulation according to claim 22 for oral administration twice daily.

42. A method of treating a bacterial infection in a patient in need thereof, which method comprises administering to said patient an effective amount of a formulation according to claim 22.

* * * * *